United States Patent
Carlson et al.

(10) Patent No.: US 11,605,467 B2
(45) Date of Patent: Mar. 14, 2023

(54) METHOD AND SYSTEM FOR AUTOMATED INCLUSION OR EXCLUSION CRITERIA DETECTION

(71) Applicant: KONINKLIJKE PHILIPS N.V., Eindhoven (NL)

(72) Inventors: Eric Thomas Carlson, New York, NY (US); Erina Ghosh, Boston, MA (US); Mohammad Shahed Sorower, Natick, MA (US); David Paul Noren, Sharon, MA (US); Bo Liu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 195 days.

(21) Appl. No.: 16/475,794

(22) PCT Filed: Jan. 3, 2018

(86) PCT No.: PCT/EP2018/050115
§ 371 (c)(1),
(2) Date: Jul. 3, 2019

(87) PCT Pub. No.: WO2018/130442
PCT Pub. Date: Jul. 19, 2018

(65) Prior Publication Data
US 2019/0355479 A1  Nov. 21, 2019

Related U.S. Application Data

(60) Provisional application No. 62/444,878, filed on Jan. 11, 2017.

(51) Int. Cl.
*G16H 50/70* (2018.01)
*G16H 10/60* (2018.01)
(Continued)

(52) U.S. Cl.
CPC ......... *G16H 50/70* (2018.01); *G06K 9/6218* (2013.01); *G16H 10/60* (2018.01); *G16H 50/20* (2018.01)

(58) Field of Classification Search
CPC ........ G16H 50/70; G16H 10/60; G16H 50/20; G06K 9/6218
See application file for complete search history.

(56) References Cited

U.S. PATENT DOCUMENTS 9,342,789 B2   5/2016  Aharoni et al.
10,198,499 B1 * 2/2019  McNair ................. G16H 15/00
(Continued)

OTHER PUBLICATIONS

International Search Report and Written Opinion, International Application No. PCT/EP2018/050115, dated Apr. 23, 2018.
(Continued)

*Primary Examiner* — Michael Tomaszewski
*Assistant Examiner* — Jay M. Patel

(57) ABSTRACT

A method (100) for training a scoring system (600) comprising the steps of: (i) providing (110) a scoring system comprising a scoring module (606); (ii) receiving (120) a training dataset comprising a plurality of patient data and treatment outcomes; (iii) analyzing (130), using a clinical decision support algorithm, the training dataset to generate a plurality of clinical decision support recommendations; (iv) clustering (140), using the scoring module, the plurality of clinical decision support recommendations into a plurality of clusters; and (v) identifying (160), using the scoring module, one or more features of at least one of the plurality of clusters, and generating, based on the identified one or more features, one or more inclusion criteria for the at least one of the plurality of clusters.

8 Claims, 6 Drawing Sheets

(51) Int. Cl.
*G16H 50/20* (2018.01)
*G06K 9/62* (2022.01)

(56) References Cited

U.S. PATENT DOCUMENTS

| | | | | |
|---|---|---|---|---|
| 10,262,103 B2* | 4/2019 | Lehrer | | G16B 20/20 |
| 11,081,206 B2 | 8/2021 | Eden | | |
| 2005/0097628 A1* | 5/2005 | Lussier | | A61P 21/00 |
| | | | | 800/260 |
| 2007/0118399 A1* | 5/2007 | Avinash | | G16H 10/60 |
| | | | | 705/2 |
| 2008/0147441 A1* | 6/2008 | Kil | | G06Q 40/08 |
| | | | | 705/2 |
| 2008/0167567 A1* | 7/2008 | Bashour | | A61B 5/352 |
| | | | | 600/521 |
| 2010/0195909 A1* | 8/2010 | Wasson | | G06F 16/313 |
| | | | | 382/176 |
| 2010/0211411 A1* | 8/2010 | Hudson | | G06Q 30/018 |
| | | | | 705/317 |
| 2011/0082712 A1* | 4/2011 | Eberhardt, III | | G16H 50/30 |
| | | | | 705/4 |
| 2011/0105466 A1* | 5/2011 | Ramsey | | G16H 20/70 |
| | | | | 514/211.13 |
| 2011/0295782 A1 | 12/2011 | Stojadinovic et al. | | |
| 2011/0307426 A1* | 12/2011 | Syed | | G16H 50/30 |
| | | | | 706/12 |
| 2012/0323132 A1* | 12/2012 | Warner | | G16H 40/63 |
| | | | | 600/509 |
| 2014/0343989 A1* | 11/2014 | Martini | | H04L 63/104 |
| | | | | 705/7.17 |
| 2015/0012222 A1* | 1/2015 | Warner | | A61B 5/316 |
| | | | | 702/19 |
| 2016/0364544 A1* | 12/2016 | Das | | A61B 5/02055 |
| 2017/0107576 A1* | 4/2017 | Babiarz | | G16B 20/00 |
| 2017/0112401 A1* | 4/2017 | Rapin | | A61B 5/7203 |
| 2018/0075194 A1* | 3/2018 | Allen | | G16H 70/20 |

OTHER PUBLICATIONS

Gonzalez et al., "Unsupervised ensemble minority clustering", Machine Learning, vol. 98, No. 1, Jul. 2013.

Xia et al., "Gathering real world evidence with cluster analysis for clinical decision support", Stud Health Technol Inform, vol. 245, Aug. 2017.

* cited by examiner

METHOD AND SYSTEM FOR AUTOMATED INCLUSION OR EXCLUSION CRITERIA DETECTION

CROSS-REFERENCE TO PRIOR APPLICATIONS

This application is the U.S. National Phase application under 35 U.S.C. § 371 of International Application No. PCT/EP2018/050115, filed on 3 Jan. 2018, which claims the benefit of U.S. Provisional Patent Application No. 62/444,878, filed on 11 Jan. 2017. These applications are hereby incorporated by reference herein.

FIELD

The present disclosure is directed generally to methods and systems for improving clinical decision support algorithms by adding a confidence score based on clustering.

BACKGROUND

A clinical decision support (CDS) system is a health information algorithm that analyzes data about a patient in view of health knowledge in order to provide information to a healthcare professional with the goal of improving health care. The information may be, for example, a diagnosis, a recommended course of action, or both. Most healthcare professionals do not simply assent to and apply the outcome of the CDS, but instead add the output of the CDS to their analysis and decision-making process, based on previous experience with the CDS. Indeed, empirical experience suggests that there are some patient features that may result in higher misclassification, including both false positive and false negative recommendations. For example, certain medications, interventions, and/or chronic conditions could lead to false recommendations of the CDS algorithm.

The output of simple CDS algorithms, including false positives and false negatives, is easily interpreted by the healthcare professional, who has a gained understanding of when the output from the CDS algorithm should be ignored, or when the response to the algorithm should be modified. However, as more complex and sophisticated CDS services are offered, it has become increasingly difficult for healthcare professionals to interpret the CDS output as confidently as was possible with simple algorithms. As a result, a healthcare professional might not fully understand when the output of the CDS algorithm should be used, trusted, or ignored. Additionally, relying on healthcare professionals to spend time interpreting the output of a complex CDS service will not only increase the already heavy workload in most healthcare settings, but will also lead to reduced confidence in the output of CDS algorithms.

SUMMARY

In view of the foregoing, it would be beneficial to provide methods and systems that improve clinical decision support algorithms to provide reliable and actionable information to healthcare professionals.

Accordingly, the present disclosure is directed to methods and systems for adding a confidence score to the output of a clinical decision support algorithm. Various embodiments and implementations herein are directed to a system that clusters the output of a CDS algorithm analyzing training data into multi-dimensional parameter space based on accuracy, and calculates a confidence score for each cluster. The confidence score for a given cluster indicates the reliability of the prediction from the CDS algorithm falling within the region of multi-dimensional parameter space corresponding to the given cluster. Once the system is trained, it receives output from a CDS algorithm, compares the output to the generated clusters, associates the output with a confidence score corresponding to the cluster to which the output falls within, and provides the confidence score to the healthcare professional.

Generally in one aspect, a method for training a score system is provided. The method includes the steps of: (i) providing a scoring system comprising a scoring module; (ii) receiving a training dataset comprising a plurality of patient data and treatment outcomes; (iii) analyzing, using a clinical decision support algorithm, the training dataset to generate a plurality of clinical decision support recommendations; (iv) clustering, using the scoring module, the plurality of clinical decision support recommendations into a plurality of clusters; and (v) identifying, using the scoring module, one or more features of at least one of the plurality of clusters, and generating, based on the identified one or more features, one or more inclusion criteria for the at least one of the plurality of clusters.

According to an embodiment, clustering is based at least in part on a comparison of each of the clinical decision support recommendations to the treatment outcomes in the training data.

According to an embodiment, the identifying step further includes generating, based on the identified one or more features, one or more exclusion criteria for the at least one of the plurality of clusters.

According to an embodiment, the method further includes the steps of: obtaining health data about a patient; analyzing, using a clinical decision support algorithm, the health data to generate a clinical decision support recommendation for the patient; assigning, using a scoring module, the clinical decision support recommendation to one of the plurality of clusters based on the extracted inclusion criteria; and assigning, using the scoring module, a confidence score to the clinical decision support recommendation based at least in part on the assignment of the recommendation to the one of the plurality of clusters.

According to an embodiment, the method further includes the step of communicating the confidence score to a user.

According to an embodiment, the confidence score is a quantitative score.

According to a second aspect, a method for training a scoring system is provided. The method includes the steps of: (i) providing a scoring system comprising a scoring module; (ii) receiving a training dataset comprising a plurality of patient data and treatment outcomes; (iii) clustering, using the scoring module, the training dataset into a plurality of clusters; (iv) analyzing, using a clinical decision support algorithm, the training dataset to generate a plurality of clinical decision support recommendations, wherein said clustering step and said analyzing step are performed separately; and (v) identifying, using the scoring module, one or more features of at least one of the plurality of clusters, and generating, based on the identified one or more features, one or more inclusion criteria for the at least one of the plurality of clusters.

According to an embodiment, the identifying step further comprises identifying the at least one of the plurality of clusters as a cluster with a plurality of false recommendations, based on the plurality of clusters compared to the plurality of clinical decision support recommendations.

According to an embodiment, the method further includes the step of identifying, using the scoring module, at least one of the plurality of clusters as a noisy cluster, wherein said identified noisy cluster is the cluster from which the one or more exclusion criteria are generated.

According to an embodiment, the analyzing step comprises the steps of analyzing, using a clinical decision support algorithm, each of the plurality of clusters individually to generate a plurality of clinical decision support recommendations for each of the plurality of clusters; and further wherein the method comprises the step of identifying, using the scoring module, at least one of the plurality of clusters with a low area under the curve score, based on least in part on the plurality of clusters and the plurality of clinical decision support recommendations.

According to an embodiment, the method further includes the steps of: (i) obtaining health data about a patient; (ii) analyzing, using a clinical decision support algorithm, the health data to generate a clinical decision support recommendation for the patient; (iii) assigning, using the scoring module, the clinical decision support recommendation to one of the plurality of clusters based on the extracted inclusion criteria; and (iv) assigning, using the scoring module, a confidence score to the clinical decision support recommendation based at least in part on the assignment of the recommendation to the one of the plurality of clusters.

According to another aspect, a method for providing a confidence score is provided. The method includes the steps of: (i) obtaining health data about a patient; analyzing, using a clinical decision support algorithm, the health data to generate a clinical decision support recommendation for the patient; assigning, using a scoring module, the clinical decision support recommendation to one of a plurality of clusters based on inclusion criteria, wherein the inclusion criteria is generated by: (i) clustering, using the scoring module, a training dataset or clinical decision support recommendations into a plurality of clusters; and (ii) identifying, using the scoring module, one or more features of at least one of the plurality of clusters, and generating, based on the identified one or more features, one or more inclusion criteria for the at least one of the plurality of clusters; assigning, using the scoring algorithm, a confidence score to the clinical decision support recommendation based at least in part on the assignment of the recommendation to the one of the plurality of clusters; and communicating the confidence score to a user.

According to an embodiment, the confidence score is a quantitative score comprising an indication of whether to utilize the clinical decision support recommendation.

As used herein for purposes of the present disclosure, the term "processor" is used generally to describe various apparatus components relating to the operation of the recommendation apparatus, system, or method. A processor can be implemented in numerous ways (e.g., such as with dedicated hardware) to perform various functions discussed herein. A "processor" can employ one or more microprocessors that may be programmed using software (e.g., microcode) to perform various functions discussed herein. A processor may also be implemented as a combination of dedicated hardware to perform some functions. Examples of processor components that may be employed in various embodiments of the present disclosure include, but are not limited to, conventional microprocessors, application specific integrated circuits (ASICs), and field-programmable gate arrays (FPGAs).

In various implementations, a processor may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects discussed herein. The terms "program" or "computer program" are used herein in a generic sense to refer to any type of computer code (e.g., software or microcode) that can be employed to program one or more processors or controllers. As used herein, the term "non-transitory machine-readable medium" will be understood to encompass both volatile and non-volatile memories, but to exclude transitory signals.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

Various embodiments may further include non-transitory computer-readable storage media, having embodied thereon a firewall program executable by a processor to perform methods described herein.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

These and other aspects will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles demonstrated herein.

DETAILED DESCRIPTION OF EMBODIMENTS

The present disclosure describes various embodiments of a method and system for providing reliable and actionable information to healthcare professionals. More generally, Applicant has recognized and appreciated that it would be beneficial to provide a method or system that augments the output of clinical decision support algorithms with a confidence score. A particular goal of utilization of certain embodiments of the present disclosure is to provide a reporting system that provides the output of a CDS algorithm and a confidence score to a healthcare professional.

In view of the foregoing, various embodiments and implementations are directed to a method and system that clusters output from a CDS algorithm analyzing training data into multi-dimensional parameter space based on accuracy, and calculates a confidence score for each cluster. The confidence score for a given cluster indicates the reliability of the prediction from the CDS algorithm falling within the region of multi-dimensional parameter space corresponding to the given cluster. The trained algorithm can then receive output from a CDS algorithm, compare the output to the generated clusters, and associate the output with a confidence score corresponding to the cluster to which the output falls within. The confidence score can then be reported to the healthcare professional, who can interpret the CDS in light of that score.

Figure 1:
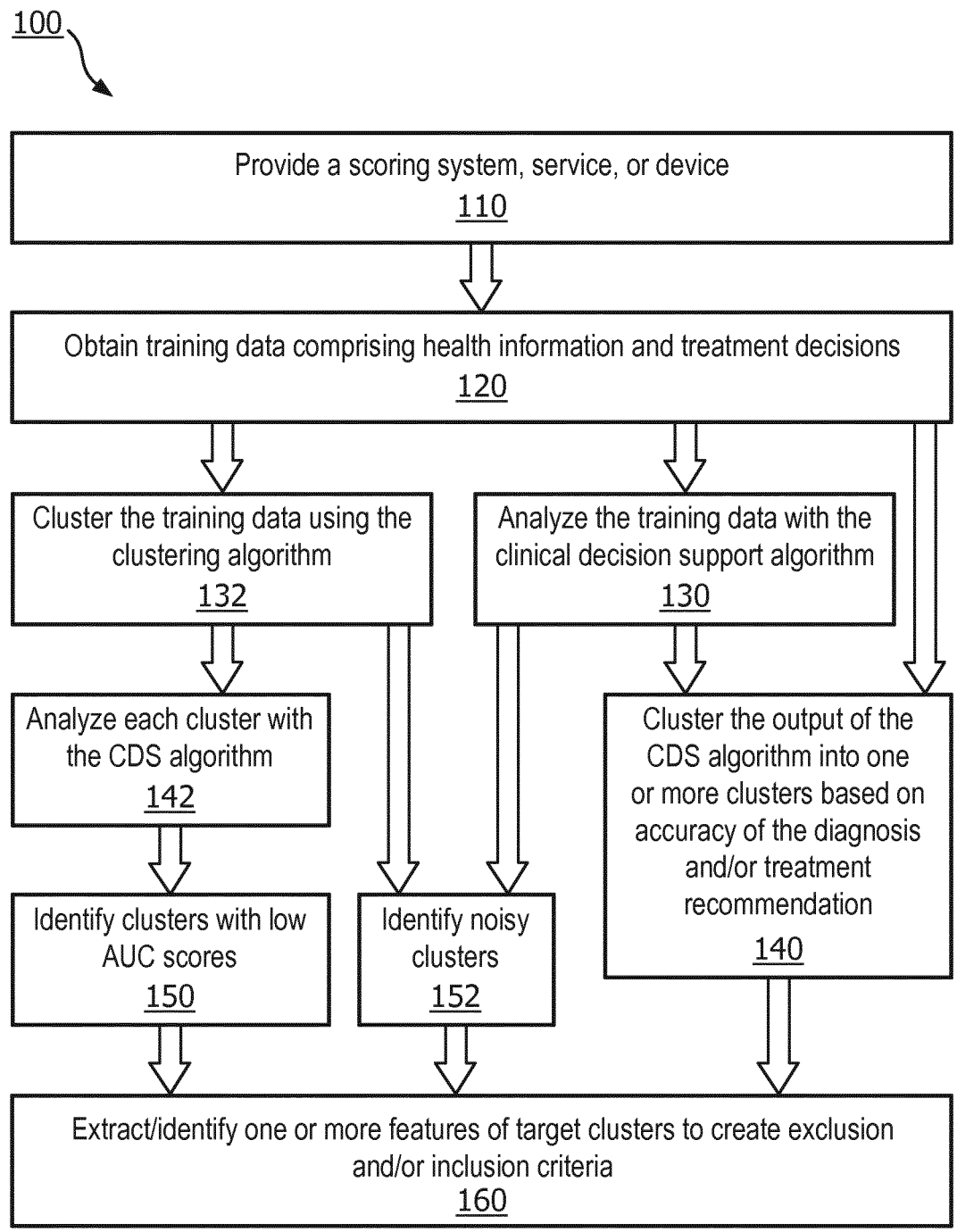
FIG. 1 is a flowchart of a method for training a clustering and scoring algorithm, in accordance with an embodiment.

Referring to FIG. 1, in one embodiment, is a method 100 for training a clustering algorithm. The method clusters the output of a CDS algorithm analyzing training data into multi-dimensional parameter space based on accuracy, and calculates a confidence score for each cluster. The confidence score for a given cluster indicates the reliability of the prediction from the CDS algorithm falling within the region of multi-dimensional parameter space corresponding to the given cluster. Once the system is trained, it associates the output of a CDS algorithm with a confidence score, and can lead to patient-centric personalized CDS healthcare output across the care continuum.

At step 110 of the method, a scoring service, system, or device is provided. The scoring service, system, or device may be any of the systems described or otherwise envisioned herein. For example, the scoring service may be a cloud-based service provided to healthcare professionals, such as a software as a service option, and can thus be hosted on one or more specialized remote servers. Alternatively, the scoring service may hosted locally to the healthcare professional, such as on a specialized computer or server at a hospital or any other healthcare setting.

At step 120 of the method, training data is obtained. The training data will be utilized to train a clustering algorithm, based on a comparison of the output of a CDS algorithm providing diagnoses and/or recommendations to actual diagnoses and/or treatment decisions. Accordingly, the training data can comprise clinical and/or non-clinical measurements or other data from patients, as well as treatment decisions and outcomes. The training data can be obtained from one or more sources, and may be generalized for all locations, settings, or one or more other variables. Alternatively, the training data may be obtained from a specific location that will be most applicable to the location where the clustering algorithm will be implemented. For example, the training data may be specific to a hospital or other healthcare facility, and/or to a physician or other healthcare professional. The training data can comprise, for example, health data, background information, demographics, and clinical measurements for a plurality of patients. Each of these patients in the training data can be associated with one or more treatment decisions that were made, as well as one or more outcomes of those treatment decisions.

At step 130 of the method, a CDS algorithm analyzes the training data to produce one or more diagnoses and/or one or more treatment recommendations. According to an embodiment, the CDS algorithm analyzing the training data is the same CDS algorithm that will be utilized by the healthcare professional in conjunction with the scoring algorithm. Alternatively, the CDS algorithm is different from the CDS algorithm that will be utilized by the healthcare professional in conjunction with the scoring algorithm. The CDS will analyze information within the training data which is normally provided to a CDS, such as health data, background information, demographics, and clinical and/or non-clinical measurements or other data about patients.

At step 140 of the method, a clustering algorithm clusters the output of the CDS algorithm. According to an embodiment, the clustering algorithm is a known clustering system, approach, or algorithm, including but not limited to K-means, spectral clustering, and other clustering approaches. The clustering algorithm can cluster the output of the CDS algorithm based on a comparison of the CDS-based diagnosis and/or recommended treatment to the known diagnosis and treatment decisions. Accordingly, the clustering algorithm may cluster the output of the CDS algorithm into groups associated with accuracy compared to the known diagnosis and treatment decisions, such as True Positive (TP), True Negative (TN), False positive (FP), and False Negatives (FN). According to an embodiment, the clusters can then optionally be fixed, such that the clustering can be validated on an independent set of patients prior to deployment.

At step 160, a clustering algorithm identifies or extracts one or more features of one or more of the clusters, where a feature is strongly correlated with the cluster. The identified or extracted features provide inclusion and exclusion criteria which can be utilized by the scoring algorithm and/or the CDS algorithm for analysis of future data. For example, identified or extracted features may be associated with the False Positive (FP) and/or False Negative (FN) cluster. According to an embodiment, the output of the clustering algorithm are clusters and one or more identified or extracted features associated with one or more of those clusters. Each cluster may be associated with a generated, identified, or extracted feature, or alternatively only one or a few of the clusters may be associated with a generated, identified, or extracted feature.

There are multiple methods for clustering, feature identification, and calculation of confidence scores. In addition to the method described above, the clustering algorithm could first be applied to the training data. Accordingly, at step 132 of the method, the clustering algorithm is applied to the given data to generate one or more clusters.

At step 142, the CDS algorithm is utilized to analyze the data within each of the clusters. Each cluster is analyzed separately. This results in an area under the curve (AUC) score for each cluster.

At step 150, clusters with low AUC scores are identified. This may be based on a learned threshold or a predetermined threshold. For example, a healthcare professional or setting may determine a particular threshold based on one or more factors internal or external factors. As an example, a hospital or healthcare professional may intentionally set a threshold very high to filter out as many false positives and/or false negatives as possible. Alternatively, the hospital or healthcare professional may intentionally set a threshold low with the understanding that there might be more false positives and/or false negatives in the output to the healthcare professional. The threshold may be a learned threshold, with a goal to make the clusters as distinct and/or reliable as possible. Accordingly, the threshold may change over time or in response to one or more internal and/or external factors.

At step 160, the scoring algorithm identifies or extracts one or more features of one or more of the clusters, where a feature is strongly correlated with the cluster. The identified or extracted features provide inclusion and exclusion criteria which can be utilized by the scoring algorithm and/or the CDS algorithm for analysis of future data.

Figure 2:
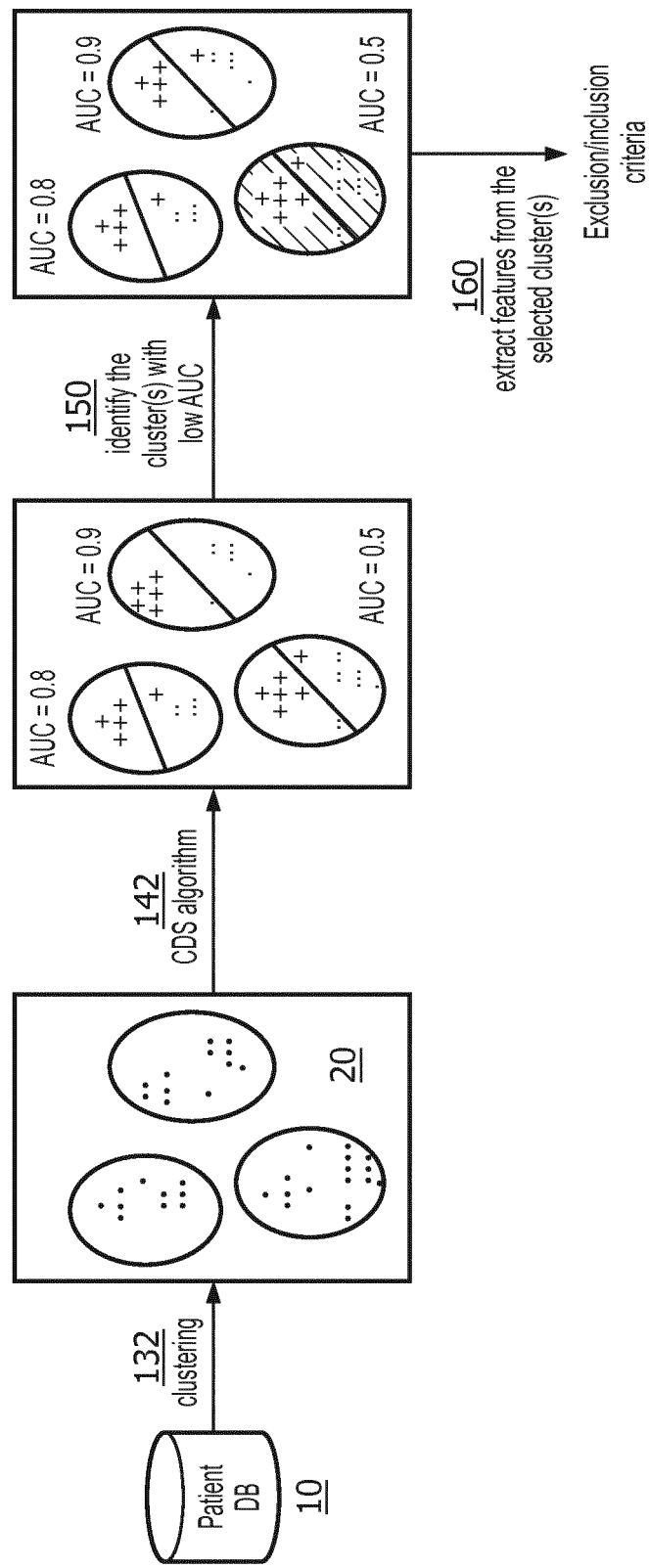
FIG. 2 is a flowchart of a method for training a clustering and scoring algorithm, in accordance with an embodiment.

Referring to FIG. 2, in one embodiment, is a schematic representation of the method described by steps 132 through 160. Training data, which can be stored in a database 10, is clustered at step 132 by a clustering algorithm, which may be a known clustering algorithm such as K-means, spectral clustering, and other clustering approaches. This results in a plurality of clusters 20. At step 142, the CDS algorithm is utilized to analyze the data within each of the clusters, resulting in an AUC score for each cluster. In FIG. 2, for example, each of the three clusters receives an AUC score, with these particular clusters receiving scores of 0.5, 0.8, and 0.9. The clusters with low AUC scores are then identified in step 150, and in step 160 one or more features are identified or extracted from one or more of the clusters in order to generate a set of exclusion and inclusion criteria which can be utilized to analyze and classify subsequent data.

As noted above, there are multiple methods for clustering, feature identification, and calculation of confidence scores. In addition to the methods described above, the CDS algorithm and the clustering algorithm could be separately applied to the training data at the same time. Accordingly, steps 130 and 132 are performed separately on the same training data. At step 130 of the method, the training data is analyzed using the CDS algorithm, and evaluate the predictions against the known labels, where each data point belongs to one of the four sets: True Positive (TP), True Negative (TN), False positive (FP), or False Negative (FN). At step 132 of the method, the training data is clustered using the clustering algorithm to divide the data into meaningful clusters. Steps 130 and 132 are either performed separately on the same training data at the same time, or at different times.

According to this embodiment, at step 152 the system utilizes the output from the CDS algorithm at step 130 and the clustering algorithm at step 132, and identifies one or more clusters with high false prediction densities, which are candidates for exclusion while the remainder are candidates for inclusion. The method then proceeds to step 160 to identify or extract one or more features from one or more of the clusters in order to generate a set of exclusion and inclusion criteria which can be utilized to analyze and classify subsequent data.

Figure 3:
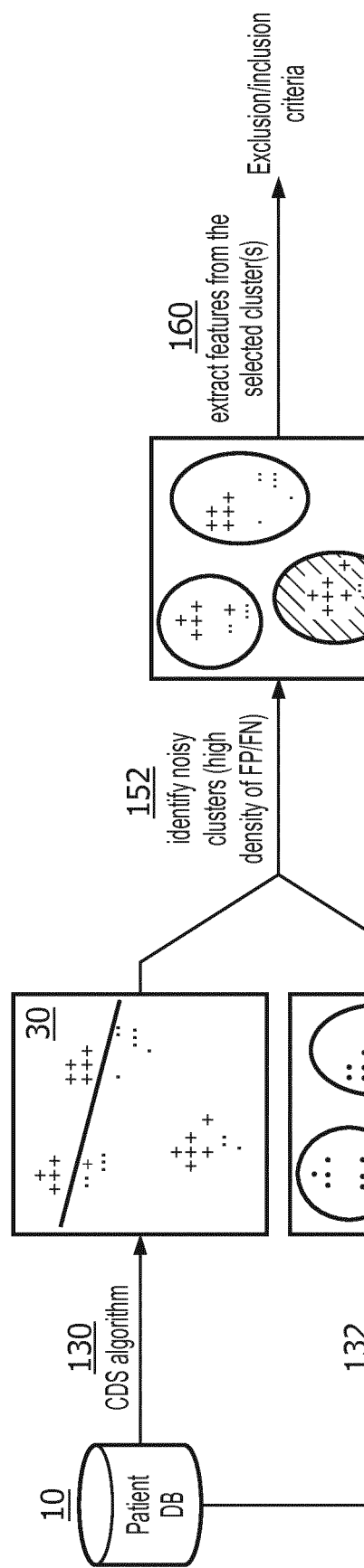
FIG. 3 is a flowchart of a method for training a clustering and scoring algorithm, in accordance with an embodiment.

Referring to FIG. 3, in one embodiment, is a schematic representation of the method described by steps 130, 132, 152, and 160 in which the CDS algorithm and the clustering algorithm are separately applied to the training data. Training data, which can be stored in a database 10, is analyzed with the CDS algorithm at step 130 to generate an output 30, and separately the training data is analyzed with the clustering algorithm to generate a plurality of clusters 20. At step 152 the system utilizes the output from the CDS algorithm at step 130 and the clustering algorithm at step 132, and identifies one or more clusters with high false prediction densities, which are candidates for exclusion while one or more of the other clusters are candidates for inclusion. At step 160, one or more features are identified or extracted from one or more of the clusters in order to generate a set of exclusion and inclusion criteria which can be utilized to analyze and classify subsequent data.

Once the clustering algorithm has created clusters and generated, identified, or extracted one or more features of these clusters to generate a set of exclusion and inclusion criteria, this resulting output can be utilized to analyze and classify subsequent data. Additionally, how well the subsequent data fits within a cluster, and thus how accurate the determination by the CDS is based on the training data, may be determined based on a confidence score which is provided to the healthcare professional.

Figure 4:
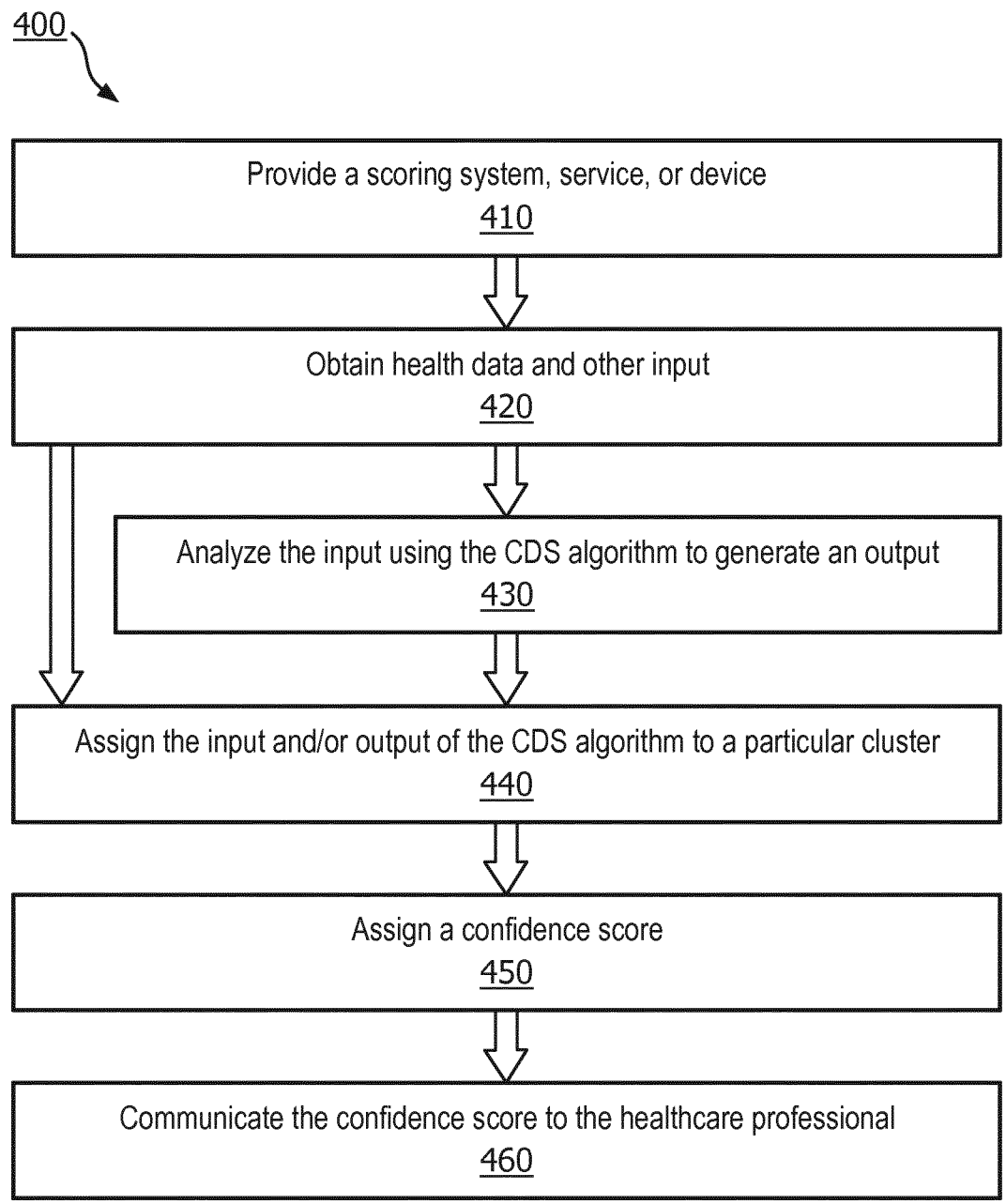
FIG. 4 is a flowchart of a method for implementing a clustering and scoring algorithm, in accordance with an embodiment.

Referring to FIG. 4, in one embodiment, is a method 400 for providing a confidence score to the output of a CDS algorithm. At step 410 of the method, the scoring service, system, or device is provided. The scoring service, system, or device may be any of the systems described or otherwise envisioned herein. For example, the scoring service may be a cloud-based service provided to healthcare professionals, such as a software as a service option, and can thus be hosted on one or more specialized remote servers. Alternatively, the scoring service may hosted locally to the healthcare professional, such as on a specialized computer or server at a hospital or any other healthcare setting.

At step 420 of the method, input to a CDS algorithm is obtained or provided. For example, the input may comprise health data, background information, demographics, clinical and/or non-clinical measurements, and/or other data from or about a patient or subject. At step 430 of the method, the CDS algorithm is applied to the input, and an output is generated. The output may be, for example, a diagnosis and/or a treatment recommendation, among other outputs of the CDS.

At step 440 of the method the scoring algorithm determines to which of the clusters, which were generated by the clustering algorithm using the training data, the output of the CDS and/or the patient data belongs. Some output of the CDS algorithm will not fit into any of the clusters, and this information could be reported to the healthcare professional.

At step 450 of the method, a confidence score is assigned to the output of the CDS algorithm, based at least in part on the cluster membership of the given patient data and/or the output of the CDS algorithm. According to an embodiment, the confidence score is quantitative and/or qualitative. For example, the confidence score can be a positive number between 0 and 1. Alternatively, the confidence score may be a "yes" or a "no." A "1" or "yes" may indicate that the output of the CDS algorithm can be utilized with confidence, while a "0" or a "no" may indicate that the output of the CDS algorithm cannot be utilized with confidence. The "0" or "no" cases may be excluded from further CDS evaluation and can be flagged to alert physicians.

Accordingly, the output of the scoring algorithm and method 400 may be, for example, a decision whether or not to utilize the CDS algorithm for a particular patient or on specific patient data. Alternatively, the output of the scoring algorithm and method 400 may be, for example, a confidence score associated with a decision whether or not to utilize the CDS algorithm. Alternatively, the output of the scoring algorithm and method 400 may be, for example, a confidence score associated the output of the CDS algorithm, enabling the healthcare professional to determine whether the CDS algorithm output is reliable.

Figure 5:
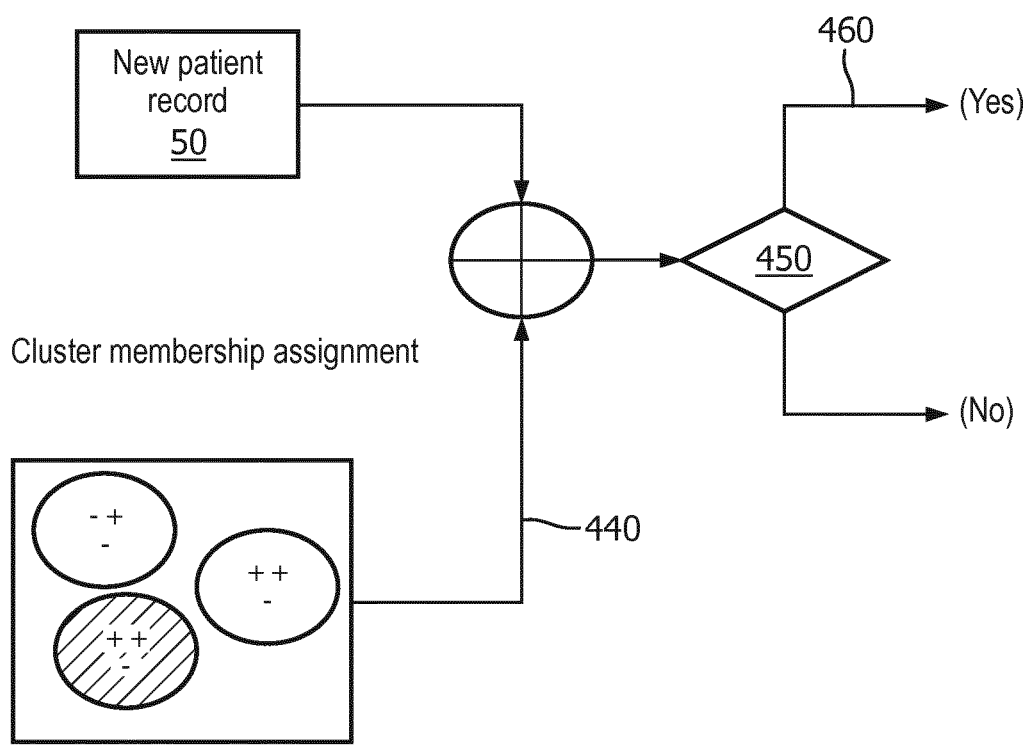
FIG. 5 is a flowchart of a method for implementing a clustering and scoring algorithm, in accordance with an embodiment.

Referring to FIG. 5, in one embodiment, is a simplified flowchart of method 400. New patient record 50 is received, and its assignment in a cluster is made at step 440 of the method. A confidence score is applied by the scoring algorithm at step 450, and at step 460 of the method the confidence score (here, a "yes" or a "no") is communicated to the healthcare professional. According to an embodiment, therefore, the output of the system is a decision whether to analyze the patient record with the CDS algorithm in association with a confidence score in that determination. According to another embodiment, the output of the system is the output of the CDS algorithm along with a confidence score in that output.

According to an embodiment, the system and method described or otherwise envisioned herein generates a generic platform capable of finding exclusion and/or inclusion criteria for any CDS algorithm. Accordingly, the system and method is not restricted to existing CDS algorithms.

Figure 6:
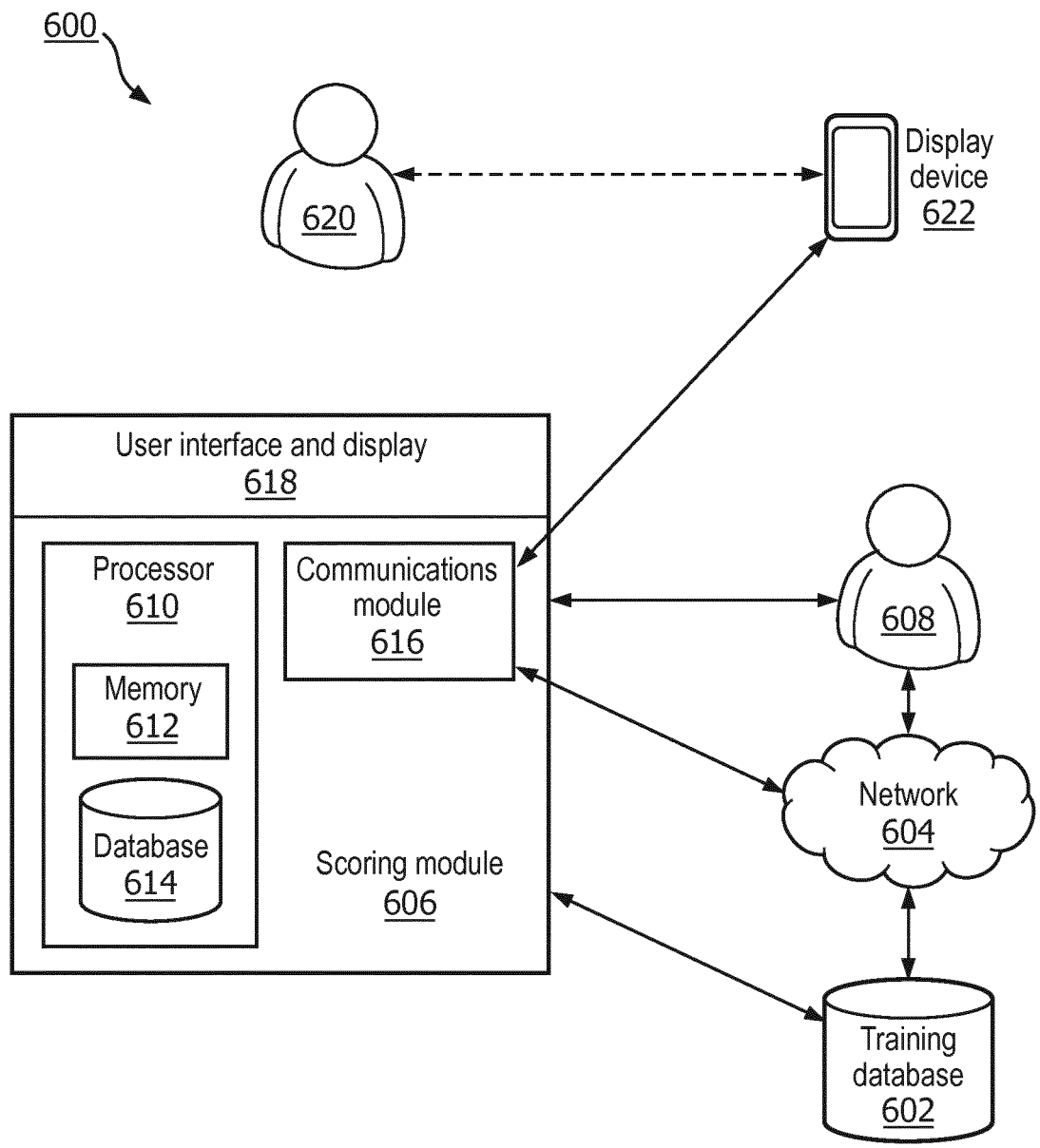
FIG. 6 is a schematic representation of a system for training and implementing a clustering and scoring algorithm, in accordance with an embodiment.

Referring to FIG. 6, in one embodiment, is a scoring system 600. The scoring service, system, or device may be any of the systems described or otherwise envisioned herein. For example, the scoring service may be a cloud-based service provided to healthcare professionals, such as a software as a service option, and can thus be hosted on one or more specialized remote servers. Alternatively, the scoring service may hosted locally to the healthcare professional, such as on a specialized computer or server at a hospital or any other healthcare setting.

According to an embodiment, scoring system 600 comprises a training database 602, which includes training data. The training data can comprise, for example, health data, background information, demographics, and clinical measurements for a plurality of patients. Each of these patients in the training data can be associated with one or more treatment decisions that were made, as well as one or more outcomes of those treatment decisions. Training database 602 may be local or remote, and thus the system may comprise a network 604 configured to communicate by wired and/or wireless communication with the scoring system.

According to an embodiment, scoring system 600 comprises a scoring module 606 which is configured to train a clustering algorithm using training data from training database 602, and which is further configured to analyze new patient data from a patient 608. According to an embodiment, scoring module 606 can comprise a processor 610 which is configured or programmed to carry out one or more processes of or for the scoring module. For example, the processor may be configured or programmed to receive and analyze the training data from training database 602, and to receive and analyze the patient data from patient 608. Processor 610 may be programmed using software to perform various functions discussed herein, and can be utilized in combination with a memory 612 and/or database 614. Memory 612 and/or database 614 can store data, including one or more commands or software programs for execution by processor 610, as well as various types of data. For example, memory 612 may comprise a non-transitory computer readable storage medium that includes a set of instructions that are executable by processor 610, and which cause the system to execute one or more of the steps of the methods described herein.

According to an embodiment, the scoring module 606 can comprise a communications module 616 to facilitate wired and/or wireless communication between the report generator and other devices and/or networks, such as network 604. Communication module 616 may be facilitated through the use of one or more antennas, for example. Communication module 616 can facilitate communication with one or more networks or with other devices, for example, by using wireless methods that are known, including but not limited to Wi-Fi, Bluetooth, 3G, 4G, LTE, and/or ZigBee, among others.

Scoring module 606 may comprise a user interface and display 618 to receive input from a healthcare provider 620, and/or to provide output or other information to healthcare provider 620. The user interface may be a button or multiple buttons, a microphone, a key stroke input, a slider, a touchscreen, or any of a variety of other inputs. The display may be, for example, an LED-based, LCD-based, or e-paper type display. In other embodiments, the display may be a touch screen display that allows the user to directly interact with a wearable device through physical contact and/or gestures.

According to an embodiment, system 600 can optionally comprise a display device 622, which may also serve as a user input device. The device 622 may be, for example, a smartphone or other portable device. According to yet another embodiment, the device 622 may be a computer such as a desktop, laptop, tablet, or other permanent or semi-permanent computing device. The device 622 may receive input from healthcare provider 620. The device 622 may also display information to healthcare provider 620 or any other intended or authorized entity.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Various embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A device for training a scoring system, the device comprising:
    a memory;
    a clustering algorithm;
    a trained scoring algorithm; and
    a processor, wherein the scoring system is trained by the processor by the steps of:
        training, using a first training dataset comprising a plurality of patient data and treatment outcomes, the clustering algorithm to generate a trained clustering algorithm, wherein the clustering algorithm is trained by comparing each of a plurality of clinical decision support recommendations generated by a trained clinical decision support algorithm to a corresponding diagnosis, treatment decision, and/or treatment outcome provided in the patient data;
        receiving a second training dataset comprising a plurality of patient data and treatment outcomes, wherein the second training dataset is a new training dataset;
        analyzing the second training dataset to generate a plurality of clinical decision support recommendations;
        clustering, using the trained clustering algorithm, the plurality of clinical decision support recommendations into a plurality of clusters, wherein clustering is based at least in part on a comparison of each of the clinical decision support recommendations to the treatment outcomes in the second training dataset;
        identifying, using the trained scoring algorithm, one or more features of at least one of the plurality of clusters, and generating, based on the identified one or more features, one or more inclusion criteria for the at least one of the plurality of clusters;
        generating, using the trained clustering algorithm and the trained scoring algorithm, one or more exclusion criteria for the at least one of the plurality of clusters, comprising: (i) identifying at least one of the plurality of clusters as a cluster with a plurality of false recommendations based on a comparison of the plurality of clusters to the plurality of clinical decision support recommendations, and (ii) identifying at least one of the plurality of clusters as a noisy cluster, and (iii) generating the one or more exclusion criteria from said identified cluster with a plurality of false recommendations and/or said identified noisy cluster.

2. A trained scoring system, comprising:
    a device for training the scoring system, wherein the device comprises a memory a clustering algorithm, a trained scoring algorithm, and a processor, and wherein the device trains the scoring system by:
        training, using a first training dataset comprising a plurality of patient data and treatment outcomes, the clustering algorithm to generate a trained clustering algorithm, wherein the clustering algorithm is trained by comparing each of a plurality of clinical decision support recommendations generated by a trained clinical decision support algorithm to a corresponding diagnosis, treatment decision, and/or treatment outcome provided in the patient data;
        receiving a second training dataset comprising a plurality of patient data and treatment outcomes, wherein the second training dataset is a new training dataset;
        analyzing the second training dataset to generate a plurality of clinical decision support recommendations;
        clustering, using the trained clustering algorithm, the plurality of clinical decision support recommendations into a plurality of clusters, wherein clustering is based at least in part on a comparison of each of the clinical decision support recommendations to the treatment outcomes in the second training dataset;
        identifying, using the trained scoring algorithm, one or more features of at least one of the plurality of clusters, and generating, based on the identified one or more features, one or more inclusion criteria for the at least one of the plurality of clusters;
        generating, using the trained clustering algorithm and the trained scoring algorithm, one or more exclusion criteria for the at least one of the plurality of clusters, comprising: (i) identifying at least one of the plurality of clusters as a cluster with a plurality of false recommendations based on a comparison of the plurality of clusters to the plurality of clinical decision support recommendations, and (ii) identifying at least one of the plurality of clusters as a noisy cluster, and (iii) generating the one or more exclusion criteria from said identified cluster with a plurality of false recommendations and/or said identified noisy cluster.

3. The device of claim 1, wherein the scoring system is further trained by the processor to perform the steps of:
obtaining health data about a patient;
analyzing, using a clinical decision support algorithm, the health data to generate a clinical decision support recommendation for the patient;
assigning the clinical decision support recommendation to one of the plurality of clusters based on the extracted inclusion criteria; and
assigning a confidence score to the clinical decision support recommendation based at least in part on the assignment of the recommendation to the one of the plurality of clusters.

4. The device of claim 3, wherein the scoring system is further trained by the processor to perform the step of communicating the confidence score to a user.

5. The device of claim 4, wherein said confidence score is a quantitative score.

6. The device of claim 5, wherein said confidence score is a quantitative score comprising an indication of whether to utilize the clinical decision support recommendation.

7. The device of claim 1, wherein said analyzing step comprises analyzing, using a clinical decision support algorithm, each of the plurality of clusters individually to generate a plurality of clinical decision support recommendations for each of the plurality of clusters; and further wherein the method comprises the step of identifying at least one of the plurality of clusters with a low area under the curve score, based on least in part on the plurality of clusters and the plurality of clinical decision support recommendations.

8. The device of claim 1, further comprising the step of:
interpreting the communicated clinical decision support recommendation in view of the communicated confidence score.

* * * * *